US00PP34018P2

(12) United States Plant Patent
van Voorst

(10) Patent No.: US PP34,018 P2
(45) Date of Patent: Mar. 15, 2022

(54) *ALSTROEMERIA* PLANT NAMED 'ZAPRIYEN'

(50) Latin Name: *Alstroemeria hybrida*
Varietal Denomination: ZAPRIYEN

(71) Applicant: Aart van Voorst, Hillegom (NL)

(72) Inventor: Aart van Voorst, Hillegom (NL)

(73) Assignee: Van Zanten Breeding B.V., Rijsenhout (NL)

( * ) Notice: Subject to any disclaimer, the term of this patent is extended or adjusted under 35 U.S.C. 154(b) by 0 days.

(21) Appl. No.: 17/331,467

(22) Filed: May 26, 2021

(30) Foreign Application Priority Data

Aug. 18, 2020 (QZ) ..... PBR 2020/1921

(51) Int. Cl.
*A01H 5/02* (2018.01)
*A01H 6/56* (2018.01)

(52) U.S. Cl.
USPC ..... Plt./309
CPC ..... *A01H 6/564* (2018.05)

(58) Field of Classification Search
USPC ..... Plt./309
CPC ..... A01H 6/564; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Alstroemeria* plant named 'ZAPRIYEN', characterized by its compact, upright to outwardly spreading and uniformly mounded plant habit; moderately vigorous to vigorous growth habit and moderate to rapid growth rate; numerous white-colored flowers with yellow-colored centers; and excellent container and garden performance.

2 Drawing Sheets

Figure 1:
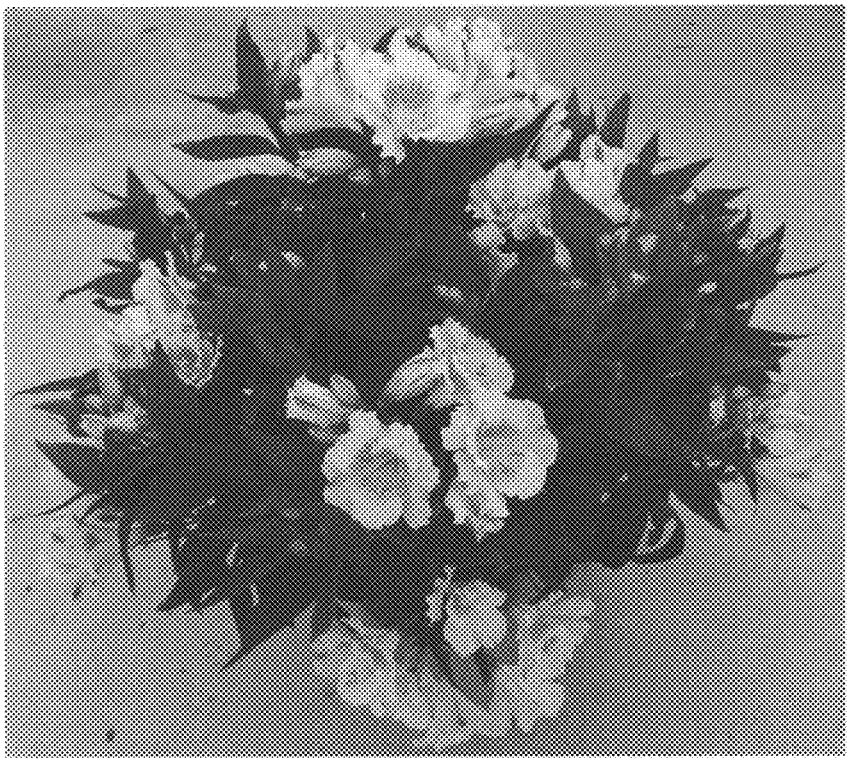

Botanical designation: *Alstroemeria hybrida.*
Cultivar denomination: 'ZAPRIYEN'.

STATEMENT REGARDING PRIOR DISCLOSURES BY INVENTOR/APPLICANT & ASSIGNEE

An European Community Plant Breeder's Rights application for the instant plant was filed by the Assignee, Van Zanten Breeding B.V. of Rijsenhout, The Netherlands, on Aug. 18, 2020, application number 2020/1921. Foreign priority is claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Alstroemeria* plant, botanically known as *Alstroemeria hybrida*, commercially used as a potted and garden-type *Alstroemeria*, and hereinafter referred to by the name 'ZAPRIYEN'.

The new *Alstroemeria* plant is a product of a planned breeding program conducted by the Inventor in Rijsenhout, The Netherlands. The objective of the breeding program is to create new potted *Alstroemeria* plants with uniform plant habit, freely flowering habit, attractive leaf and flower coloration and good garden performance.

The new *Alstroemeria* plant originated from a cross-pollination made by the Inventor in Rijsenhout, The Netherlands in June, 2013 of a proprietary *Alstroemeria hybrida* selection identified as code number 113371-1, not patented, as the female, or seed, parent with a proprietary *Alstroemeria hybrida* selection identified as code number 115184-1, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in June, 2014.

Asexual reproduction of the new *Alstroemeria* plant by rhizome divisions in a controlled greenhouse environment in Rijsenhout, The Netherlands since September, 2014 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'ZAPRIYEN'. These characteristics in combination distinguish 'ZAPRIYEN' as a new and distinct *Alstroemeria* plant:

1. Compact, upright to outwardly spreading and uniformly mounded plant habit.
2. Moderately vigorous to vigorous growth habit and moderate to rapid growth rate.

3. Numerous white-colored flowers with yellow-colored centers.
4. Excellent container and garden performance.

Plants of the new *Alstroemeria* can be compared to plants of the female parent selection. Plants of the new *Alstroemeria* differ from plants of the female parent selection primarily in flower color as plants of the new *Alstroemeria* have white-colored flowers with yellow-colored centers whereas plants of the female parent selection have solid white-colored flowers.

Plants of the new *Alstroemeria* can be compared to plants of the male parent selection. Plants of the new *Alstroemeria* differ from plants of the male parent selection primarily in flower color as plants of the new *Alstroemeria* have white-colored flowers with yellow-colored centers whereas plants of the male parent selection have yellow-colored flowers.

Plants of the new *Alstroemeria* can be compared to plants of *Alstroemeria hybrida* 'Zapriclair', disclosed in U.S. Plant Pat. No. 25,588. In side-by-side comparisons, plants of the new *Alstroemeria* differ primarily from plants of 'Zapriclair' in flower size as plants of the new *Alstroemeria* have smaller flowers than plants of 'Zapriclair'. In addition, flowers of plants of the new *Alstroemeria* have larger yellow-colored centers than flowers of plants of 'Zapriclair'.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet (FIG. 1) is a side perspective view of a typical flowering plant of 'ZAPRIYEN' grown in a container.

Figure 2:
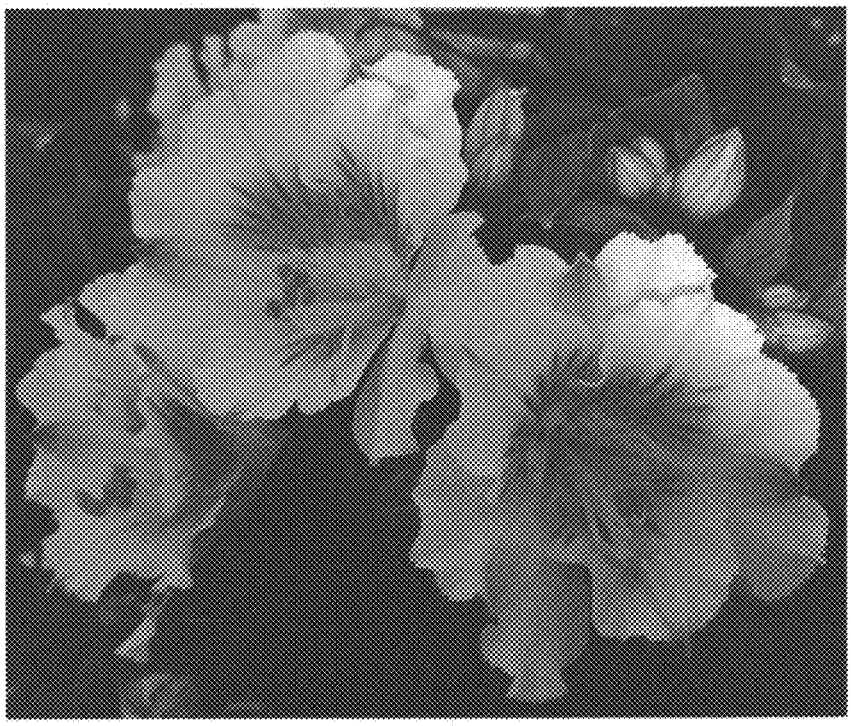

The photograph on the second sheet (FIG. 2) is a close-up view of typical flowers and flower buds of 'ZAPRIYEN'.

DETAILED BOTANICAL DESCRIPTION

The aforementioned photographs and following observations and measurements describe plants of the new *Alstroemeria* grown during the spring in 14-cm containers in a glass-covered greenhouse in Rijsenhout, The Netherlands. During the production of the plants, day temperatures ranged from 15° C. to 25° C., night temperatures ranged from 10° C. to 15° C., soil temperatures averaged 14° C. and light levels averaged 5,000 lux. Plants were three months old when the photographs and description were taken. In the following description, color references are made to The Royal Horticultural Society Colour Chart, 2015 Edition, except where general terms of ordinary dictionary significance are used.

Botanical classification: *Alstroemeria hybrida* 'ZAPRIYEN'.

Parentage:

*Female, or seed, parent.*—Proprietary *Alstroemeria hybrida* selection identified as code number 113371-1, not patented.

*Male, or pollen, parent.*—Proprietary *Alstroemeria hybrida* selection identified as code number 115184-1, not patented.

Propagation:

*Type.*—In vitro rhizogenesis.

*Time to produce a rooted young plant, summer.*—About 40 days at temperatures of 16° C. to 25° C.

*Time to produce a rooted young plant, winter.*—About 60 days at temperatures of 16° C. to 20° C.

*Root description.*—Fibrous, fleshy, thick; color, close to 155D.

*Rooting habit.*—Freely branching; medium density.

*Rhizomes.*—Shape: Elongate; rounded. Length: About 10 cm to 30 cm. Diameter: About 3 mm to 10 mm. Texture and luster: Smooth; matte. Color: Close to 155D.

Plant description:

*Plant and growth habit.*—Compact, upright to outwardly spreading and uniformly mounding plant habit; freely branching habit with about five to six primary lateral branches developing per plant, dense and bushy appearance; moderately vigorous to vigorous growth habit; and moderate to rapid growth rate.

*Plant height.*—About 35 cm.

*Plant diameter (spread).*—About 48 cm to 50 cm.

Lateral branch description:

*Length.*—About 30 cm.

*Diameter.*—About 6 mm.

*Internode length.*—About 4 mm.

*Strength.*—Moderately strong, flexible.

*Aspect.*—About 45° from vertical.

*Texture and luster.*—Smooth, glabrous; semi-glossy.

*Color, developing and developed.*—Close to 138B.

Leaf description:

*Arrangement.*—Alternate; simple.

*Length.*—About 8.5 cm to 9.5 cm.

*Width.*—About 2 cm to 3 cm.

*Shape.*—Lanceolate.

*Apex.*—Acute.

*Base.*—Cuneate.

*Margin.*—Entire.

*Texture and luster, upper surface.*—Moderately rugose, glabrous; semi-glossy.

*Texture and luster, lower surface.*—Ribbed, glabrous; matte.

*Aspect.*—Upright to horizontal, twisting.

*Venation pattern.*—Parallel.

*Color.*—Developing leaves, upper surface: Close to NN137A. Developing leaves, lower surface: Close to 137B. Fully expanded leaves, upper surface: Close to NN137A; venation, close to 145A. Fully expanded leaves, lower surface: Close to 137D; venation, close to 145B.

*Petioles.*—Length: About 1.5 cm. Diameter: About 6 mm. Texture and luster: Smooth, glabrous; semi-glossy. Strength: Moderately strong, flexible. Color, upper surface: Close to 138D. Color, lower surface: Close to 139D.

Flower description:

*Flower type and habit.*—Single cup-shaped flowers arranged in compound umbels; flowers face upright to outwardly; perianth segments separate; freely flowering habit with about five to six flowers per inflorescence and about 200 flower buds and flowers developing per plant.

*Natural flowering season.*—Flowering continuous from the spring until the autumn in The Netherlands; early flowering habit, plants begin flowering about 70 to 80 days after planting.

*Fragrance*.—None detected.

*Flower longevity on the plant*.—About 1.5 weeks; flowers not persistent.

*Flower buds*.—Length: About 3.5 cm. Diameter: About 2 cm. Shape: Roughly ovoid. Texture and luster: Smooth, glabrous; matte. Color: Close to 155A with stripes, close to 141B.

*Umbel height*.—About 13.5 cm.

*Umbel diameter*.—About 13 cm.

*Flower diameter*.—About 5 cm by 6 cm.

*Flower depth*.—About 6 cm.

*Perianth*.—Arrangement: Six arranged in two whorls, each whorl with two lateral and one median segments. Inner perianth, lateral segments: Length: About 5 cm. Width: About 2.5 cm. Shape: Oblanceolate. Apex: Wishbone-shaped and acuminate. Base: Attenuate. Margin: Distally, dentate and proximally, entire; undulate. Texture and luster, upper surface: Smooth, glabrous; semi-glossy. Texture and luster, lower surface: Ribbed; semi-glossy. Color, when opening and fully opened, upper surface: Towards the apex and base, close to NN155A; center, close to 13B with small to medium-sized stripes, close to N167B; midvein, close to N138A; color does not change with subsequent development. Color, when opening and fully opened, lower surface: Towards the apex and base, close to NN155A; center, close to 13C with faint stripes; midvein, close to 143B; color does not change with subsequent development. Inner perianth, median segment: Length: About 4.8 cm. Width: About 2.5 cm. Shape: Oblanceolate. Apex: Wishbone-shaped and acuminate. Base: Attenuate. Margin: Distally, dentate and proximally, entire; undulate. Texture and luster, upper surface: Smooth, glabrous; semi-glossy. Texture and luster, lower surface: Ribbed; semi-glossy. Color, when opening and fully opened, upper surface: Towards the apex and base, close to NN155A; center, close to 13B with small to medium-sized stripes, close to N167B; midvein, close to N138A; color does not change with subsequent development. Color, when opening and fully opened, lower surface: Towards the apex and base, close to NN155A; center, close to 13C with faint stripes; midvein, close to 143B; color does not change with subsequent development. Outer perianth, lateral segments: Length: About 5.5 cm. Width: About 3.5 cm. Shape: Obovate. Apex: Embedded point. Base: Attenuate. Margin: Entire; undulate. Texture and luster, upper surface: Ribbed, glabrous; semi-glossy. Texture and luster, lower surface: Ribbed, glabrous; matte. Color, when opening and fully opened, upper surface: Close to NN155A; apex, close to N138B; color does not change with subsequent development. Color, when opening and fully opened, lower surface: Towards the apex and base, close to NN155A; center, close to 13D; apex, close to 143A; midvein, close to 143A; color does not change with subsequent development. Outer perianth, median segment: Length: About 5.5 cm. Width: About 3.5 cm. Shape: Obovate. Apex: Embedded point. Base: Attenuate. Margin: Entire; undulate. Texture and luster, upper surface: Ribbed, glabrous; semi-glossy. Texture and luster, lower surface: Ribbed, glabrous; matte. Color, when opening and fully opened, upper surface: Close to NN155A; apex, close to N138B; color does not change with subsequent development. Color, when opening and fully opened, lower surface: Towards the apex and base, close to NN155A; center, close to 13D; apex, close to 143A; midvein, close to 143A; color does not change with subsequent development.

*Pedicels*.—Length: About 2.5 cm. Diameter: About 1.5 mm to 2.5 mm. Strength: Strong. Angle: About 30° from branch axis. Texture and luster: Smooth, glabrous; semi-glossy. Color: Close to 138B.

*Reproductive organs*.—Stamens: Quantity per flower: Typically six. Filament length: About 3.5 cm. Filament color: Close to 155A. Anther length: About 8 mm. Anther width: About 2 mm. Anther shape: Elliptical. Anther color: Close to 160C. Pollen amount: Abundant. Pollen color: Close to 163B. Pistils: Quantity per flower: One. Pistil length: About 4.5 cm. Style length: About 3 cm. Style color: Close to 155A. Stigma diameter: About 1 cm. Stigma shape: Three-parted. Stigma color: Close to 155A. Ovary color: Close to 138A.

*Fruits and seeds*.—To date, fruit and seed development have not been observed on plants of the new *Alstroemeria*.

Pathogen & pest resistance: To date, plants of the new *Alstroemeria* have not been observed to be resistant to pathogens and pests common to *Alstroemeria* plants.

Garden performance: Plants of the new *Alstroemeria* have been observed to have excellent garden performance and to tolerate wind, rain, temperatures from about −5° C. to about 40° C. and to be suitable for USDA Hardiness Zone 9.

It is claimed:

1. A new and distinct *Alstroemeria* plant named 'ZAPRIYEN' as illustrated and described.

* * * * *